United States Patent [19]
Ueno et al.

[11] Patent Number: 5,973,126
[45] Date of Patent: Oct. 26, 1999

[54] AZO COMPOUNDS AND PROCESS FOR PRODUCING THE SAME

[75] Inventors: Ryuzo Ueno, Nishinomiya; Masaya Kitayama, Takarazuka; Kenji Minami, Sennan; Hiroyuki Wakamori, Hyogo, all of Japan

[73] Assignee: Kabushiki Kaisha Ueno Seiyaku Oyo Kenkyujo, Osaka, Japan

[21] Appl. No.: 09/068,954

[22] PCT Filed: Oct. 9, 1997

[86] PCT No.: PCT/JP97/03637

§ 371 Date: May 20, 1998

§ 102(e) Date: May 20, 1998

[87] PCT Pub. No.: WO98/16587

PCT Pub. Date: Apr. 23, 1998

[30] Foreign Application Priority Data

Oct. 11, 1996 [JP] Japan .................................. 8-269985

[51] Int. Cl.$^6$ ........................... C09B 29/20; C09D 11/00; C08J 3/20
[52] U.S. Cl. ......................... 534/656; 534/581; 534/720; 534/602; 534/801; 534/863; 534/865; 534/866; 534/867; 534/874; 534/DIG. 4; 106/31.77; 106/31.78; 106/31.8; 106/496; 524/84; 524/93; 524/94; 524/102; 524/190

[58] Field of Search ..................... 534/656, 720, 534/801, 863, 865, 866, 867; 106/496, 31.77, 31.78, 31.8

[56] References Cited

U.S. PATENT DOCUMENTS

| 3,523,934 | 8/1970 | Haubrich et al. | 534/720 |
| 3,591,576 | 7/1971 | Haubrich | 534/720 |
| 3,609,134 | 9/1971 | Mory | 534/801 X |
| 3,821,191 | 6/1974 | Ruider et al. | 534/801 X |
| 4,115,055 | 9/1978 | Kirner et al. | 534/863 X |
| 4,737,581 | 4/1988 | Hari | 534/867 |

FOREIGN PATENT DOCUMENTS

| 51-119719 | 10/1976 | Japan . |
| 56-100859 | 8/1981 | Japan . |
| 57-10649 | 1/1982 | Japan . |

*Primary Examiner*—Fiona T. Powers
*Attorney, Agent, or Firm*—Sughrue, Mion, Zinn, Macpeak & Seas, PLLC

[57] ABSTRACT

A monoazo compound synthesized using 2-hydroxynaphthalene-3,6-dicarboxylic acid (or salt thereof), an amide, an ureide or an ester thereof as a coupler is novel, and is superior in water resistance, chemical resistance and solvent resistance. The present invention provides such a novel azo compound and a process for producing the same.

9 Claims, 2 Drawing Sheets

AZO COMPOUNDS AND PROCESS FOR PRODUCING THE SAME

TECHNICAL FIELD

The present invention relates to a novel azo compound and a process for producing the same.

BACKGROUND OF THE INVENTION

Azo pigments are synthesized by the coupling reaction of a diazonium compound and a coupler. Among the couplers used in the coupling reaction, a particularly important coupler is 2-hydroxynaphthalene-3-carboxylic acid or a derivative thereof.

Brilliant Carmine 6B (Pigment Red 57) and Watchung Red (Pigment Red 48) which are prepared from 2-hydroxynaphthalene-3-carboxylic acid are most important red azolake pigments. These are used in the form of an insoluble metallic lake such as Ca, Ba, Mn, etc., but is inherently unstable to an acid or alkali because of metallic salts.

On the other hand, an insoluble azo pigment is synthesized using, as a coupler, 2-hydroxynaphthalene-3-anilide synthesized by the condensation of 2-hydroxynaphthalene-3-carboxylic acid and anilines. This so-called naphthol pigment has been developed for the purpose of improving the solubility and fastness, and is generally superior to an azolake pigment in properties such as light resistance, weathering resistance, chemical resistance, solvent resistance, etc.

Furthermore, an azo pigment derived from 2-hydroxynaphthalene-6-carboxylic acid which is an isomer of 2-hydroxynaphthalene-3-carboxylic acid, and characteristics thereof are known (Japanese Patent Kokai Publication No. Hei 2-302471).

DISCLOSURE OF THE INVENTION

The present invention is characterized by obtaining a novel azo coloring material, which is superior in water resistance, chemical resistance, solvent resistance, etc.

The present invention provides a novel azo compound using 2-hydroxynaphthalene-3,6-dicarboxylic acid, an ester, an amide or an ureide derivatives as a coupler, a coloring material containing the same, and a process for producing the above azo compound. That is, the present invention relates to the azo compound represented by the following general formula [I]:

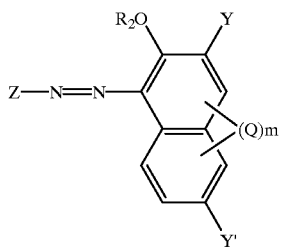

[I]

[wherein Y represents —(CONH)n—X or —COR;
Y' represents —(CONH)n—X or —COR';
(X and X' may be the same or different and represent an optionally substituted aromatic group, or an optionally substituted heterocyclic group having a conjugated double bond);

R and R' may be the same or different and represent a hydroxyl group, an optionally branched alkoxy group having 1 to 6 carbon atoms, a benzyloxy group, a phenyloxy group or a phenacyloxy group (provided that an acceptable salt may be formed when any one of R and R' is a hydroxyl group);

n represents an integer of 1 or 2;

$R_2$ represents a hydrogen atom, an optionally branched alkyl group having 1 to 6 carbon atoms, an acyl group having 1 to 6 carbon atoms or a phenylalkyl group;

Q represents an optionally branched alkyl group having 1 to 6 carbon atoms, an optionally branched alkoxyl group having 1 to 6 carbon atoms, a halogen atom, a nitro group or a nitroso group; m represents an integer of 0 to 3 (when m is 1, Q may be combined with any one of two condensed rings and, when m is 2 or 3, Q may be combined with one or both condensed rings or may be combined together with two condensed rings to form a ring); and Z represents an optionally substituted monovalent aromatic group], a process for producing the same, and a coloring material containing this azo compound. The coloring material in the present specification means a dye, a pigment, ink, paint, printing ink, an electrocharge generating material, etc.

The present invention also relates to a process for producing an azo compound represented by the following general formula [I]:

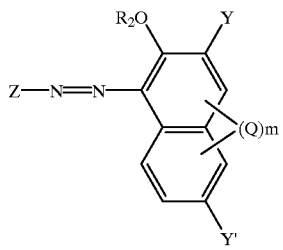

[I]

[wherein Y represents —(CONH)n—X or —COR;
Y' represents —(CONH)n—X' or —COR';
(X and X' may be the same or different and represent an optionally substituted aromatic group, or an optionally substituted heterocyclic group having a conjugated double bond);

R and R' may be the same or different and represent a hydroxyl group, an optionally branched alkoxy group having 1 to 6 carbon atoms, a benzyloxy group, a phenyloxy group or a phenacyloxy group;

n represents an integer of 1 or 2;

$R_2$ represents a hydrogen atom, an optionally branched alkyl group having 1 to 6 carbon atoms or an acyl group having 1 to 6 carbon atoms or a phenylalkyl group;

Q represents an optionally branched alkyl group having 1 to 6 carbon atoms, an optionally branched alkoxyl group having 1 to 6 carbon atoms, a halogen atom, a nitro group or a nitroso group; m represents an integer of 0 to 3 (when m is 1, Q may be combined with any one of two condensed rings and, when m is 2 or 3, Q may be combined with one or both condensed rings or may be combined together with two condensed rings to form a ring); and Z represents an optionally substituted monovalent aromatic group], which comprises diazotizing aromatic amines represented by the following general formula [II]:

Z—NH$_2$ [II]

[wherein Z represents an optionally substituted monovalent aromatic group] and coupling the resulting diazonium compound with a compound represented by the following formula [III]:

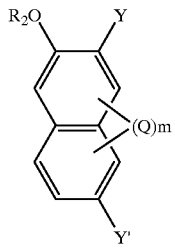

[III]

[wherein Y represents —(CONH)n—X or —COR;
Y' represents —(CONH)n—X' or —COR';
(X and X' may be the same or different and represent an optionally substituted aromatic group, or an optionally substituted heterocyclic group having a conjugated double bond);
R and R' may be the same or different and represent a hydroxyl group, an optionally branched alkoxy group having 1 to 6 carbon atoms, a benzyloxy group, a phenyloxy group or a phenacyloxy group;
n represents an integer of 1 or 2; and
R$_2$ represents a hydrogen atom, an optionally branched alkyl group having 1 to 6 carbon atoms or an acyl group having 1 to 6 carbon atoms or a phenylalkyl group);
Q represents an optionally branched alkyl group having 1 to 6 carbon atoms, an optionally branched alkoxyl group having 1 to 6 carbon atoms, a halogen atom, a nitro group or a nitroso group; m represents an integer of 0 to 3 (when m is 1, Q may be combined with any one of two condensed rings and, when m is 2 or 3, Q may be combined with one or both condensed rings or may be combined together with two condensed rings to form a ring)].

In the present invention, as described above, a coupler (compound represented by the general formula [III]) is prepared from 2-hydroxynaphthalene-3,6-dicarboxy amide, ureide or carboxylate derivative as a raw material. 2-Hydroxynaphthalene-3,6-dicarboxylic acid as the raw material can be obtained by the Kolbe-Schmitt process of reacting carbon dioxide with potassium 2-naphtholate at high temperature under high pressure in the presence of a potassium salt such as potassium phenolate, etc.

The amide or ureide can be obtained by preparing acid chloride from thionyl chloride in a solvent such as sulfolane according to a usual process and reacting the resulting acid chloride with amines or ureas. Alternatively, it can be obtained by reacting amines or ureas directly with phosphorous trichloride or dicyclohexylcarbodiimide.

The amines or ureas, namely compounds constituting a group X or X' in Y or Y', include optionally substituted aromatic amino compounds such as aniline (X or X' is a phenyl group), α- or β-aminonaphthalene (X or X' is a naphthyl group) and aminoanthraquinone (X or X' is an anthraquinonyl group); optionally substituted heterocyclic compounds having a conjugated double bond, such as aminobenzimidazolone (X or X' is a benzimidazolonyl group), aminocarbazole (X or X' is a carbazolyl group), aminopyridine (X or X' is a pyridyl group), aminothiazole (X or X' is a thiazolyl group), aminbbenzothiazole (X or X' is a benzothiazolyl group) and arninoimidazole (X or X' is an imidazolyl group); and aminoindole (X or X' is an indolyl group), aminothiophene (X or X' is a thionyl group), aminophenothiazine (X or X' is a phenothiazinyl group), aminoacridine (X or X' is an acridinyl group) and aminoquinoline (X or X' is a quinolinyl group). The substituent of these compounds includes halogen, nitro group, lower alkyl group, lower alkoxy group, cyano group, phenoxy group, amide group (e.g. phenylaminocarbonyl group, etc.) and these phenoxy group and amide groups include other substituents such as halogen, lower alkyl, lower alkoxy, alkylaminosulfonyl, nitrile, etc.

A corresponding urea can be obtained by reacting the above amino compound with a potassium cyanate. Namely, for example, phenyl urea may be obtained from an aniline.

Y and Y' may represent —COR or —COR'. R and R' may be the same or different and represent a hydroxyl group, an optionally branched alkoxy group having 1 to 6, preferably 1 to 4 carbon atoms, particulary a methoxy group, an ethoxy group; a benzyloxy group, a phenoxy group or phenacyloxy group. An aromatic ring contained in these groups may have a substituent such as halogen atom, lower alkyl group, etc.

The group R2 is a hydrogen atom, an optionally branched alkyl group having 1 to 6, preferably 1 to 4 carbon atoms, particularly a methyl group, an ethyl group; an acyl group having 1 to 6, preferably 1 to 4 carbon atoms, particularly an acetyl group; or a phenylalkyl group. The phenylalkyl group may have a substituent such as halogen atom, lower alkyl group, etc.

The group Q may have a substituent on a naphthalene nucleus, and examples thereof include optionally branched alkyl group having 1 to 6, preferably 1 to 4 carbon atoms, particularly methyl group, ethyl group; optionally branched alkoxy group having 1 to 6, preferably 1 to 4 carbon atoms, particularly methoxy group, ethoxy group; halogen atom, nitro group or nitroso group. The number of the substituent m is normally 0, but may be up to 3. Provided that there is no case of having a substituent at the 1-position of the naphthalene nucleus. Furthermore, when m is 1, Q may be combined with any one of two condensed rings. When m is 2 or 3, Q may be combined with one or both of the condensed rings, or may be combined together with the two condensed rings to form a ring.

The azo compound of the present invention can be obtained by diazotizing aromatic amines represented by the general formula [II] with sodium nitrite, etc., and coupling the resulting diazonium compound with the above 2-hydroxynaphthalene-3,6-dicarboxylic acid and a derivative thereof (e.g. carboxyamide or carboxyureide, or ester thereof).

Furthermore, it can be obtained by forming a lake by using an appropriate metallic salt, e.g. salt of Ca, Ba, Mn, Sr, etc., when R or R' is a hydroxyl group.

Aromatic amines, namely compounds constituting Z in an azo group, include monoamino condensed polycyclic hydrocarbons such as aniline (Z is a phenyl group), α- or β-naphthylamine (Z is a naphthyl group), monoaminoanthracene (Z is an anthryl group), monoaminoindene (Z is an indenyl group) and monoaminofluolenon (Z is a fluolenyl group); and monoarninoindole (Z is an indolyl group), monoaminobenzothiophene (Z is a benzothionyl group), monoaminoquinoline (Z is a quinolinyl group) and monoaminocarbazole (Z is a carbazolyl group). These aromatic amines may have a substituent, and examples of the substituent include halogen, lower alkyl (particularly methyl), cyano, nitro, lower alkoxy group, amido group, sulfo-group, alkylaminosulfonyl group, aminocarbonyl group, phenoxy group, alkoxycarbonyl group, hydroxy group, benzoylamino group, etc.

Most preferred aromatic amines are optionally substituted anilines (Z is a phenyl group) or optionally substituted α- or β-naphthylamines (Z is a naphthyl group).

The process of obtaining a diazonium compound from amines is not specifically limited. A general process of diazotizing aromatic primary amines with sodium nitrite may be used.

The diazonium compound is further coupled with the above-described 2-hydroxynaphthalene-3,6-dicarboxyamide, carboxyureide or an ester thereof, but this method may be a conventional method.

The azo compound of the present invention can be used in a pigment, printing ink, paint, a colorating agent for plastics, etc.

The following Examples further illustrate the present invention in detail hereinafter.

EXAMPLE 1

Synthesis of 2-hydroxy-1-(2'-methyl-5'-nitrophenylazo)-3,6-bisphenylaminocarbonylnaphthalene

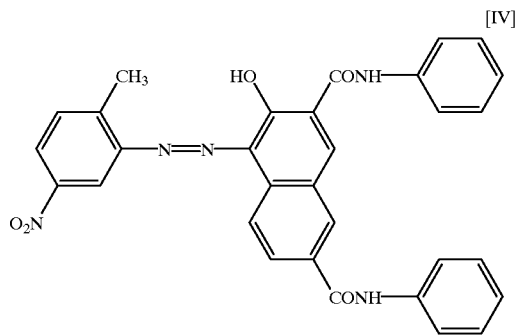

[IV]

As an amine component, 4.6 g of 2-methyl-5-nitroaniline was suspended in 100 g of water and 4.0 g of 35% hydrochloric acid was added to dissolve the amine component. Then, a solution obtained by dissolving 2.3 g of sodium nitrite in 10 g of water with maintaining at 0° C. was added dropwise to perform diazotization. On the other hand, as a coupler component, 9.6 g of 2-hydroxy-3,6-bisphenylaminocarbonylnaphthalene was suspended in 190 g of methanol and a solution obtained by dissolving 2.0 g of sodium hydroxide in 10 g of water was added to the suspension to dissolve the coupler component and the solution was maintained at 15° C. The coupling reaction was carried out by adding above diazonium solution to this coupler solution over about 20 minutes. Further, after stirring for 30 minutes, 100 g of water was added to the resulting solution to raise the temperature to 70° C. and then 600 g of water was added dropwise over about 1 hour. After cooling slowly to room temperature, the resulting solution was suction-filtrated. The product was subjected to ultrasonic cleaning and then dried under reduced pressure to obtain 8.2 g of a bright yellowish red powder [2-hydroxy-1-(2'-methyl-5'-nitrophenylazo)-3,6-bisphenylaminocarbonylnaphthalene](melting point·decomposition point: 331.2° C. (with decomposition)).

An infrared absorption spectrum (KBr method) is shown in FIG. 1.

Various properties such as water resistance, chemical resistance, solvent resistance, migration resistance and light resistance as a baked paint of the azo compound obtained in Example 1, a 2-hydroxy-3-phenylaminocarbonyl derivative (Comparative Example 1) as a commercially available product and a 2-hydroxy-6-phenylaminocarbonyl derivative (Comparative Example 2) described in Japanese Patent Kokai Publication No. Hei 2-302471 are shown in Table 1.

TABLE 1

| | Amine (upper)/coupler (lower) | Structural formula of azo compound | Color shade | Water resistance | Chemical resistance HCl | Chemical resistance NaOH | Solvent resistance acetone | Solvent resistance methanol | Solvent resistance xylene | Migration resistance (1% vs PVC) | Light resistance (baked paint) |
|---|---|---|---|---|---|---|---|---|---|---|---|
| Example 1 | 2-methyl-5-nitroaniline 2-hydroxy-3,6-bisphenylaminocarbonyl-naphthalene | | Bright yellowish red | A | A | A | A | A | A | B | A |
| Comp. Example 1 | 2-methyl-5-nitroaniline 2-hydroxy-3-phenylaminocarbonyl-naphthalene | | Slightly yellowish red | B | A | B | E | D | C | C | C |
| Comp. Example 2 | 2-methyl-5-nitroaniline 2-hydroxy-6-phenylaminocarbonyl-naphthalene | | Vivid orange | A | A | A | B | A | A | B | D |

The water resistance, chemical resistance and solvent resistance were evaluated as follows.

Water resistance: 1 Part of a sample was added to 20 parts of water and dispersed by an ultrasonic wave for 20 minutes. After boiling for 1 minute, the resulting solution was cooled and filtrated. Then, the color of the filtrate was observed and evaluated according to the following criteria A to E.

Chemical resistance: 1 Part of a sample was added to 20 parts of each 5% solution of hydrochloric acid or sodium hydroxide and dispersed by an ultrasonic wave for 5 minutes. After filtrating, the color of the filtrate was observed and evaluated according to the following criteria A to E.

Solvent resistance: 1 Part of a sample was added to 20 parts of acetone or methanol or xylene and dispersed by an ultrasonic wave for 5 minutes. After filtrating, the color of the filtrate was observed and evaluated according to the following criteria A to E.

| | |
|---|---|
| None coloring is observed. | A |
| Very slight coloring is observed. | B |
| Some coloring is observed. | C |
| Marked coloring is observed. | D |
| Drastic coloring is observed. | E |

The migration resistance was evaluated as follows.
1) To 100 parts of a compound of 100 parts of soft polyvinyl chloride, 50 parts of dioctyl phthalate, 2 parts of tin maleate, 0.4 parts of calcium stearate and 0.6 parts of barium stearate, 1 part of a sample is added, followed by kneading at 140° C. for 5 minutes in a twin-roll mill and further pressurization at 100 kgf/cm$^2$ to obtain a test piece having a thickness of 1 mm.
2) The test piece obtained in the item 1) is cut into pieces of 40 mm×50 mm in size.
3) 100 Parts of the compound obtained in the item 1) and 5 parts of titanium white are processed in the same manner as in the item 1) and then cut into pieces of 40 mm×60 mm in size.
4) The test piece of the item 2) is laminated on the sheet of the item 3) and a load is applied so that 100 gf/cm$^2$ is obtained.
5) The laminate of the item 4) is allowed to stand at 70° C. for 24 hours. The degree of color migration to the titanium white sheet is evaluated according to the following criteria.

| | |
|---|---|
| None migration: | A |
| Some migration: | B |
| Marked migration: | C |
| Drastic migration: | D |

The light resistance as baked paint was evaluated as follows.
1) 1.0 Parts of a sample, 0.7 parts of dioctyl phthalate and 0.7 parts of castor oil are kneaded by using a Hoover Muller (100 revolutions×3 times).
2) To 1.0 parts of the mixture obtained by kneading in the item 1), 10.0 parts of a curing agent Beckosol (ER-3653-60) and 0.1 parts of manganese naphthenate are added, followed by sufficient kneading on a glass plate by using a spatula.
3) The sample obtained in the item 2) is applied on a steel plate in a thickness of 0.5 mil (1.27×10$^{-5}$ m), followed by heating at 145° C. for 30 minutes using an air dryer to obtain a test piece of baked paint.
4) A half of the piece of the item 3) is masked and exposed to light for 100 hours using a weathermeter (manufactured by Shimadzu Corp.: Suntester XF-180•xenon lamp). The masked portion and non-masked portion are measured, respectively, and evaluation is performed by a color difference ΔE between them.

| | |
|---|---|
| ΔE = not more than 2 | A |
| ΔE = 2 to 3 | B |
| ΔE = 3 to 5 | C |
| ΔE = 5 to 8 | D |
| ΔE = not less than 8 | E |

EXAMPLE 2

Synthesis of 2-hydroxy-1-(2'-methyl-5'-nitrophenylazo)-3,6-bis(2'-methylphenylaminocarbonyl)naphthalene

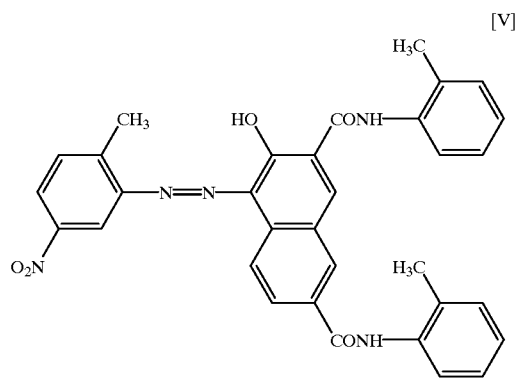

[V]

According to the same manner as described in Example 1 except for replacing 2-hydroxy-3,6-bisphenylaminocarbonylnaphthalene of Example 1 by 14.3 g of 2-hydroxy-3,6-bis(2'-methylphenylaminocarbonyl)naphthalene as a coupler component, 9.2 g of an yellowish red powder [2-hydroxy-1-(2'-methyl-5'-nitrophenylazo)-3,6-bis(2'-methylphenylaminocarbonyl)naphthalene] was obtained (melting point·decomposition point: 307.0° C. (with decomposition).

EXAMPLE 3

Synthesis of 2-hydroxy-1-(2'-methyl-5'-nitrophenylazo)-3,6-bis(2'-methoxylphenylaminocarbonyl)naphthalene

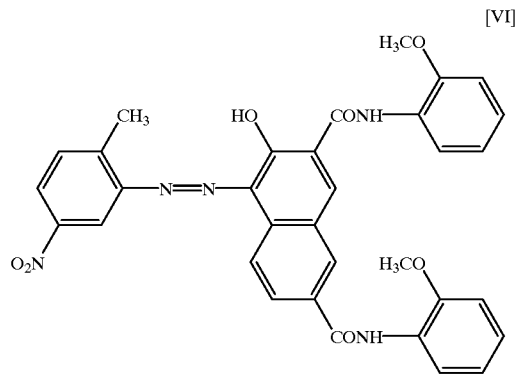

[VI]

According to the same manner as described in Example 1 except for replacing 2-hydroxy-3,6-bisphenylaminocarbonylnaphthalene of Example 1 by 15.1 g of 2-hydroxy-3,6-bis(2'-methoxyphenylaminocarbonyl) naphthalene as a coupler component, 9.4 g of a bluish red powder [2-hydroxy-1-(2'-methyl-5'-nitrophenylazo)-3,6-bis(2'-methoxyphenylaminocarbonyl)naphthalene] was obtained (melting point·decomposition point: 293.5° C. (with decomposition).

EXAMPLE 4

Synthesis of 2-hydroxy-1-(2'-methoxy-5'-phenylaminocarbonylphenylazo)-3,6-bisphenylaminocarbonylnaphthalene

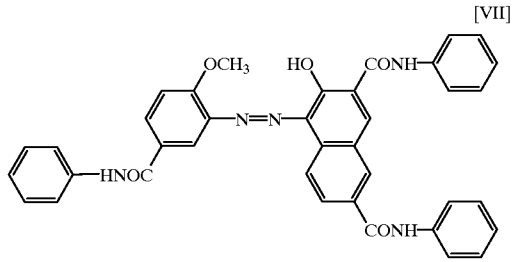

[VII]

According to the same manner as described in Example 1 except for replacing 2-methyl-5-nitroaniline of Example 1 by 7.3 g of 2-methoxy-5-phenylaminocarbonylaniline as an amine component and dispersing it in 50 g of water and 50 g of methanol, 6.8 g of a bluish red powder [2-hydroxy-1-(2'-methoxy-5'-phenylaminocarbonylphenylazo)-3,6-bisphenylaminocarbonylnaphthalene] was obtained (melting point·decomposition point: 282.5° C. (with decomposition).

EXAMPLE 5 TO 22

According to the same manner as described in Example 1 except for replacing 2-methyl-5-nitroaniline of Example 1 by an amine shown in Table 2 as an amine component and dispersing it in 50 g of water and 50 g of methanol, and replacing 2-hydroxy-3,6-bisphenylaminocarbonylnaphthalene by a coupler shown in Table 2 as a coupler component, azo compounds were synthesized. The melting point·decomposition point of synthesized azo compounds are shown in Table 2.

TABLE 2

| Example No. | Amine (upper)/ Coupler (lower) | Structural formula of azo compound | Color shade | Melting point/ decomposition point |
|---|---|---|---|---|
| 5 | 2-methoxy-5-phenylamino-carbonylaniline 2-hydroxy-3,6-bis(3'-nitrophenyl-aminocarbonyl)-naphthalene | [XVIII] | Bright bluish red | 294° C. (with decomposition) |
| 6 | 2-methoxy-5-phenylamino-carbonylaniline 2-hydroxy-3,6-bis(5'-diethyl-aminosulfonyl-2'-methoxyphenyl-aminocarbonyl)-naphthalene | [XIX] (Et = $C_2H_5$) | Dark bluish red | 312.7° C. |

TABLE 2-continued

| Example No. | Amine (upper)/ Coupler (lower) | Structural formula of azo compound | Color shade | Melting point/ decomposition point |
|---|---|---|---|---|
| 7 | 2-methoxy-5-phenylamino-carbonylaniline 2-hydroxy-3,6-bis(1'-naphthyl-aminocarbonyl)-naphthalene | [XX] | Bright bluish red | 325.4° C. |
| 8 | 2-methoxy-5-phenylamino-carbonylaniline 3,6-bis(benz-imidazolon-5-yl-aminocarbonyl)-2-hydroxy-naphthalene | [XXI] | Dark brownish red | 354.1° C. |

TABLE 2-continued

| Example No. | Amine (upper)/ Coupler (lower) | Structural formula of azo compound | Color shade | Melting point/ decomposition point |
|---|---|---|---|---|
| 9 | 2-methoxy-5-phenylaminocarbonylaniline 2-hydroxy-3,6-bis-(anthraquinon-2'-ylaminocarbonyl)-naphthalene | [XXII] | Dark bluish red | 324.6° C. (with decomposition) |
| 10 | 2-methoxycarbonylaniline 2-hydroxy-3,6-bis(3'-nitrophenyl-aminocarbonyl)-naphthalene | [XXIII] | Brownish red | 357.1° C. (with decomposition) |

TABLE 2-continued

| Example No. | Amine (upper)/ Coupler (lower) | Structural formula of azo compound | Color shade | Melting point/ decomposition point |
|---|---|---|---|---|
| 11 | 2-methoxy-carbonylaniline 2-hydroxy-3,6-bis-(2',5'-dimethoxy-4'-phenylamino-carbonyl-phenyl-aminocarbonyl)-naphthalene | [XXIV] | Brownish orange | 319.2° C. (with melting) |
| 12 | 2-methoxy-carbonylaniline 2-hydroxy-3,6-bis(4'-phenoxy-carbonyl)-naphthalene | [XXV] | Bright yellowish red | 288.6° C. (with melting) |

TABLE 2-continued

| Example No. | Amine (upper)/ Coupler (lower) | Structural formula of azo compound | Color shade | Melting point/ decomposition point |
|---|---|---|---|---|
| 13 | 2-methoxy-carbonylaniline 3,6-bis(benz-imidazolon-5-yl-aminocarbonyl)-2-hydroxy-naphthalene | [XXVI] | Brown | 341.0° C. (with decomposition) |
| 14 | 2-methoxy-5-diethylamino-sulfonylaniline 2-hydroxy-3,6-bisphenylamino-carbonyl-naphthalene | [XXVII] (Et = $C_2H_5$) | Yellowish red | 305.8° C. (with melting) |

TABLE 2-continued

| Example No. | Amine (upper)/ Coupler (lower) | Structural formula of azo compound | Color shade | Melting point/ decomposition point |
|---|---|---|---|---|
| 15 | 2-methoxy-5-diethylamino-sulfonylaniline / 2-hydroxy-3,6-bis(5'-chloro-2',4'-dimethoxy-phenylamino-carbonyl)-naphthalene | [XXVIII] (Et = C₂H₅) | Bluish red | 304.1° C. (with melting) |
| 16 | 4-chloro-2-methylaniline / 2-hydroxy-3,6-bisphenylamino-carbonyl-naphthalene | [XXIX] | Dark yellowish red | 278.0° C. (with melting) |

TABLE 2-continued

| Example No. | Amine (upper)/ Coupler (lower) | Structural formula of azo compound | Color shade | Melting point/ decomposition point |
|---|---|---|---|---|
| 17 | 4-chloro-2-methylaniline / 2-hydroxy-3,6-bis(2'-ethoxyphenylaminocarbonyl)-naphthalene | 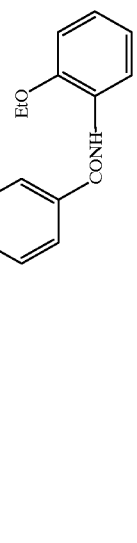 [XXX] | Yellowish red | 266.6° C. (with melting) |
| 18 | 4-chloro-2-methoxylaniline / 3,6-bis(benzimidazolon-5-yl-aminocarbonyl)-2-hydroxynaphthalene | 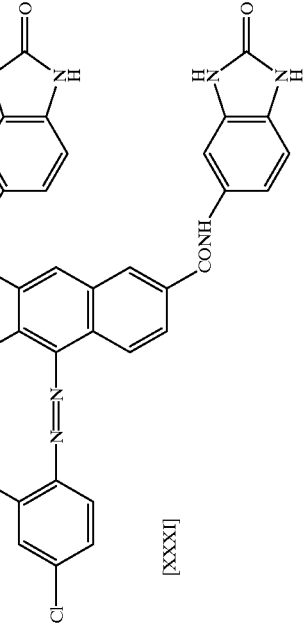 [XXXI] | Dark bluish red | 328.9° C. (with decomposition) |

TABLE 2-continued

| Example No. | Amine (upper)/ Coupler (lower) | Structural formula of azo compound | Color shade | Melting point/ decomposition point |
|---|---|---|---|---|
| 19 | 2-methyl-5-nitroaniline 3,6-bis(benzimidazolon-5-yl-aminocarbonyl)-2-hydroxynaphthalene | [XXXII] | Dark brownish purple | 334.6° C. (with decomposition) |
| 20 | 2-methyl-5-nitroaniline 2-hydroxy-3,6-bis(2'-chlorophenylureidocarbonyl)-naphthalene | [XXXIII] | Bright brownish red | 239.4° C. (with decomposition) |

TABLE 2-continued

| Example No. | Amine (upper)/ Coupler (lower) | Structural formula of azo compound | Color shade | Melting point/ decomposition point |
|---|---|---|---|---|
| 21 | 4-chloro-2-methoxyaniline 2-hydroxy-3,6-bis-(2'-chloro-phenylureido-carbonyl)-naphthalene | [XXXIV] | Dark purple | 260.2° C. (with decomposition) |
| 22 | 2,5-dichloroaniline 2-hydroxy-3,6-bis-(2'-chloro-phenylureido-carbonyl)-naphthalene | [XXXV] | Brownish red | 231.5° C. (with decomposition) |

EXAMPLE 23

Synthesis of calcium salt of 2-hydroxy-3,6-dihydroxycarbonyl-1-(4'-methyl-2'-sulfo-phenylazo)-naphthalene

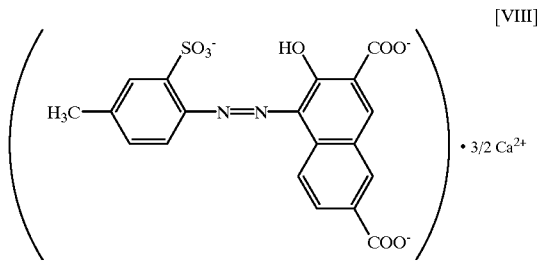

[VIII]

5.0 g of 4-aminotoluene-3-sulfonic acid (4B-Acid) was dispersed in 250 g of water and 5.4 g of 35% hydrochloric acid was added to dissolve. Then, diazotization was carried out by adding dropwise the solution, obtained by dissolving 2.1 g of sodium nitrite in 10 g of water with maintaining at 0° C., over about 20 minutes. On the other hand, 6.4 g of 2-hydroxy-3,6-dihydroxycarbonylnaphthalene was suspended in 200 g of N-methyl-2-pyrrolidone and 200 g of water and 38.5 g of 10% sodium hydroxide solution, and then 24.0 g of 5% rosin solution were added. After dissolving them, the solution was maintained at 13 (±2) ° C. To this solution, the diazonium solution described above was added dropwise over about 30 minutes and the solution was further stirred for 90 minutes. After adjusting the pH of the reaction solution to 9.0 to 9.5, this solution was added dropwise to the solution obtained by dissolving 6.7 g of calcium chloride dihydrate in 125 g of water to form a lake. After 30 minutes, the temperature was raised to 70° C. The resulting solution was allowed to stand for about 30 minutes and then cooled slowly to room temperature. Thereafter, 200 g of water was added to the solution, followed by suction filtration. The product was washed with water and then dried to obtain 10.3 g of a deep red powder [calcium salt of 2-hydroxy-3,6-dihydroxycarbonyl-1-(4'-methyl-2'-sulfo-phenylazo) naphthalene (melting point·decomposition point: 406.1° C. (with decomposition)).

An infrared absorption spectrum (KBr method) is shown in FIG. 2.

EXAMPLE 24

Synthesis of a calcium salt of 1-(5'-chloro-4'-methyl-2'-sulfo-phenylazo)-2-hydroxy-3,6-dihydroxycarbonyl-naphthalene

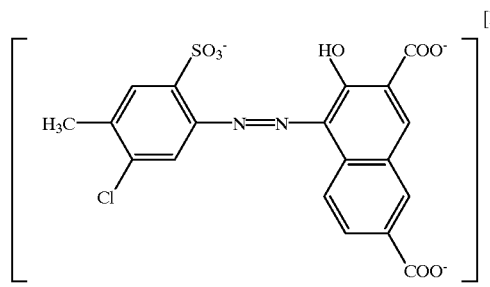

[IX]

According to the same manner as described in Example 23 except for replacing 4-aminotoluene-3-sulfonic acid (4B-Acid) of Example 23 by 5.9 g of 4-amino-2-chlorotoluene-5-sulfonic acid (2B-Acid), 11.3 g of a deep red powder [calcium salt of 1-(5'-chloro-4'-methyl-2'-sulfo-phenylazo)-2-hydroxy-3,6-dihydroxycarbonylnaphthalene] was obtained (melting point·decomposition point: 446.7° C. (with decomposition).

EXAMPLE 25

(1) Synthesis of 2-hydroxy-3,6-bis(2'-pyridylaminocarbonyl)naphthalene

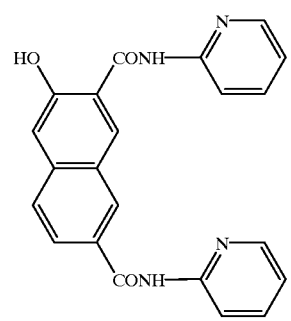

[X]

14.3 g of 2-hydroxy-3,6-dihydroxycarbonylnaphthalene and 13.6 g of 2-aminopyridine were dissolved in 120 g of N-methyl-2-pyrrolidone, and 150 g of ethyl acetate and then 30.9 g of dicyclohexylcarbodiimide were added to this solution and the reaction was performed at room temperature for about 15 hours. After insoluble matters were removed by filtration, the filtrate was concentrated to about half of the weight, and then 30.6 g of diglyme was added and the temperature is raised to 170° C. After 2 hours, the solution was cooled to room temperature and insoluble matters were removed by filtration. The filtrate was concentrated and 200 g of ethyl acetate was added, and then the crystal deposited after an ultrasonic treatment was filtered. The product was dried to obtain 15.7 g of an yellowish white crystal [2-hydroxy-3,6-bis(2'-pyridylaminocarbonyl) naphthalene] (melting point: 311.2° C.).

(2) Synthesis of 2-hydroxy-1-(5'-diethylaminosulfonyl-2'-methoxyphenylazo)-3,6-bis(2'-pyridylaminocarbonyl)-naphthalene

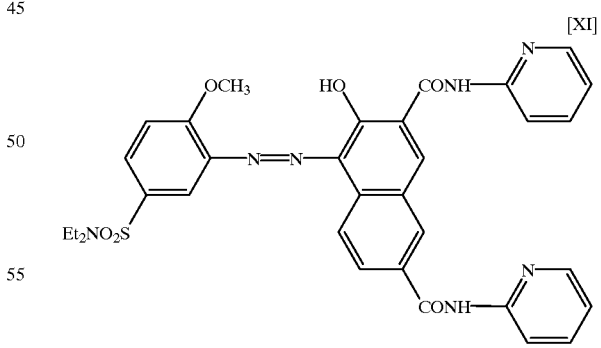

[XI]

According to the same manner as described in Example 1 except for replacing 2-methyl-5-nitroaniline of Example 1 by 7.8 g of 5-diethylaminosulfonyl-2-methoxyaniline as an amine component and dispersing it in 50 g of water and 50 g of methanol, and replacing 2-hydroxy-3,6-bisphenylaminocarbonylnaphthalene by 9.6 g of 2-hydroxy-3,6-bis(2'-pyridylaminocarbonyl)naphthalene synthesized in above (1) as a coupler component, 7.1 g of an brownish red product [2-hydroxy-1-(5'-diethylaminosulfonyl-2'-methoxyphenylazo)-3,6-bis(2'-pyridylaminocarbonyl)naphthalene] was obtained (melting point·decomposition point: 197.6° C. (with decomposition)).

EXAMPLE 26

Synthesis of 2-hydroxy-3,6-bis(thiazol-2'-ylaminocarbonyl)naphthalene

[XII]

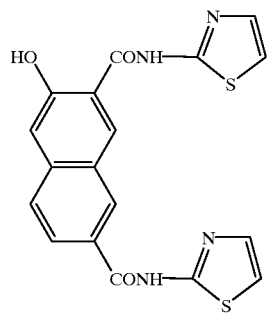

In 50.0 g of N-methyl-2-pyrrolidone and 30.0 g of toluene, 6.3 g of 2-aminothiazole was dissolved and heated to 60° C. To this solution, a solution obtained by dissolving 5.6 g of 2-hydroxy-3,6-bischlorocarbonylnaphthalene in 120.0 g of N-methyl-2-pyrrolidone was added and the temperature was raised to 80° C. After about 24 hours, the solution was concentrated and 470 g of water was added. The deposited crystal was filtered, washed with methanol and then dried to obtain 1.7 g of a flesh color crystal [2-hydroxy-3,6-bis(thiazol-2'-ylaminocarbonyl)naphthalene] (melting point: 286.6° C.).

EXAMPLE 27

(1) Synthesis of 2-hydroxy-3,6-bis(benzothiazol-2'-ylaminocarbonyl)naphthalene

[XIII]

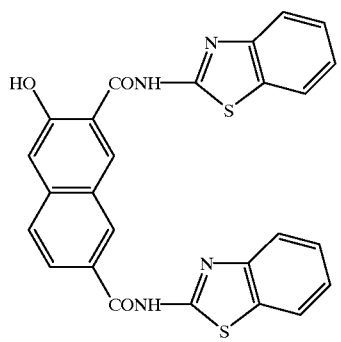

According to the same manner as described in Example 26 except for replacing 2-aminothiazole of Example 26 by 9.4 g of 2-aminobenzothiazole, 1.9 g of a flesh color crystal [2-hydroxy-3,6-bis(benzothiazol-2'-ylaminocarbonyl)naphthalene] was obtained (melting point: 364.1° C.).

(2) Synthesis of 2-hydroxy-1-(2'-methoxy-5'-phenylaminocarbonylphenyl)azo-3,6-bis(benzothiazol-2"-ylaminocarbonyl)naphthalene

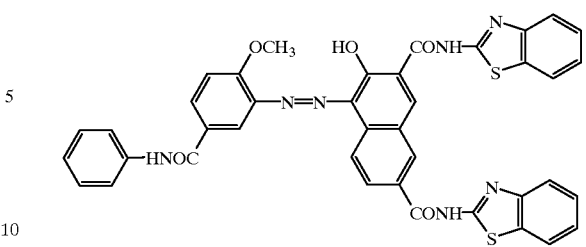

As an amino component, 1.46 g of 2-methoxy-5-phenylaminocarbonylaniline was dispersed in 20 g of water and 1.8 g of 35% hydrochloric acid is added. Then, the solution prepared by dissolving 0.84 g of sodium nitrite in 5 g of water with maintaining at the temperature of 0° C. was added dropwise to the dispersion solution to perform diazotization. Then, 4 g of borofluoric acid was added and a deposited diazonium salt was filtered.

On the other hand, as a coupler component, 1.19 g of 2-hydroxy-3,6-bis(benzothiazol-2'-ylamninocarbonyl)naphthalene was dissolved in 20 g of N-methyl-2-pyrrolidone and 0.25 g of sodium methoxide was added. After dissolving, the solution was maintained at the temperature of 15° C. The coupling reaction was carried out by adding the solution, prepared by dissolving the diazonium salt described above in 15 g of N-methyl-2-pyrrolidone, to this solution over about 20 minutes. After stirring for 1 hour or more, 0.22 g of acetic acid was added and then 50 g of methanol was slowly added. The product was obtained by suction filtration, washed with methanol using an ultrasonic wave, and then dried under reduced pressure to obtain 1.17 g of a dark red powder [2-hydroxy-1-(2'-methoxy-5'-phenylaminocarbonylphenyl)azo-3,6-bis(benzothiazol-2"-ylaminocarbonyl)naphthalene] (melting point·decomposition point: 316.3° C. (with decomposition)).

EXAMPLE 28

(1) Synthesis of 2-hydroxy-3,6-bis(4',5'-dicyanoimidazol-2'-ylaminocarbonyl)naphthalene

[XIV]

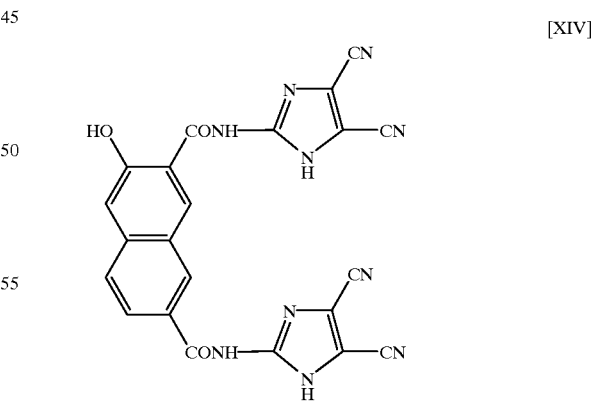

According to the same manner as described in Example 26 except for replacing 2-aminothiazole of Example 26 by 8.3 g of 2-amino-4,5-dicyanoimidazole, 3.5 g of a flesh color crystal [2-hydroxy-3,6-bis(4',5-'-dicyanoimidazol-2'-ylaminocarbonyl)-naphthalene] was obtained (melting point: 256.8° C.).

(2) Synthesis of 2-hydroxy-1-(2'-methoxy-5'-phenylaminocarbonylphenyl)azo-3,6-bis(4",5"-dicyanoimidazol-2"-ylaminocarbonyl)naphthalene

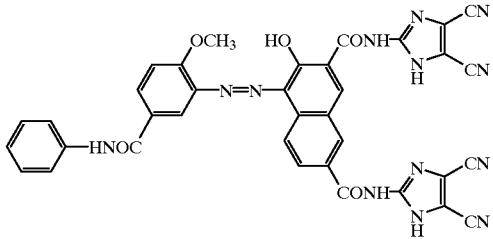

According to the same manner as described in Example 27(2) except for replacing 2-hydroxy-3,6-bis(benzothiazol-2'-ylaminocarbonyl)naphthalene of Example 27(2) by 1.49 g of 2-hydroxy-3,6-bis(4',5'-dicyanoimidazol-2'-ylaminocarbonyl)naphthalene as a coupler component, 0.83 g of a dark red powder [2-hydroxy-1-(2'-methoxy-5'-phenylaminocarbonylphenyl)azo-3,6-bis(4",5"-dicyanoimidazol-2"-ylaminocarbonyl)naphthalene] was obtained (melting point·decomposition point: 320.6° C. (with decomposition)).

EXAMPLES 29 TO 73

According to the same manner as described in Example 23 except for replacing 4-aminotoluene-3-sulfonic acid of Example 23 by the amines shown in Table 3 as an amine component, and replacing 2-hydroxy-3,6-dihydroxycarbonylnaphthalene by the couplers shown in Table 3 as a coupler component, and exchanging the usage of calcium chloride dihydrate into 1.1 to 1.2-fold equivalent weight, azo compounds were synthesized. In Examples 40, 41 and 42, barium chloride, strontium chloride, manganese chloride were used respectively in place of calcium chloride in Example 23. The melting point and decomposition point of the resulting azo compounds are shown in Table 3.

TABLE 3

| Example No. | Amine (upper)/Coupler (lower) | Structural formula of azo compound | Color shade | Melting point/ decomposition point |
|---|---|---|---|---|
| 29 | aniline / 2-hydroxy-3,6-dihydroxycarbonylnaphthalene | | Yellowish red | 363.9° C. (with decomposition) |
| 30 | aniline / 2-hydroxy-3-hydroxycarbonyl-6-phenylaminocarbonylnaphthalene | | Yellowish red | 529.1° C. (with decomposition) |
| 31 | aniline / 2-hydroxy-3-hydroxycarbonyl-6-(5'-chloro-2',4'-dimethoxyphenylaminocarbonyl)naphthalene | | Brownish red | 518.5° C. (with decomposition) |

TABLE 3-continued

| Example No. | Amine (upper)/Coupler (lower) | Structural formula of azo compound | Color shade | Melting point/ decomposition point |
|---|---|---|---|---|
| 32 | 4-aminotoluene-3-sulfonic acid / 2-hydroxy-3,6-dihydroxycarbonylnaphthalene | [structure with 3/2 Ca²⁺] | Reddish purple | 352.3° C. (with decomposition) |
| 33 | 4-aminotoluene-3-sulfonic acid / 2-hydroxy-3-hydroxycarbonyl-6-phenylaminocarbonylnaphthalene | [structure with Ca²⁺] | Reddish purple | 395.2° C. (with decomposition) |
| 34 | 4-aminotoluene-3-sulfonic acid / 2-hydroxy-3-hydroxycarbonyl-6-(5'-chloro-2',4'-dimethoxyphenylaminocarbonyl)naphthalene | [structure with Ca²⁺] | Reddish purple | 467.9° C. (with decomposition) |

TABLE 3-continued

| Example No. | Amine (upper)/Coupler (lower) | Structural formula of azo compound | Color shade | Melting point/decomposition point |
|---|---|---|---|---|
| 35 | 4-aminotoluene-3-sulfonic acid --------- 2-hydroxy-3-hydroxycarbonyl-6-(3'-nitrophenyl-aminocarbonyl)naphthalene | 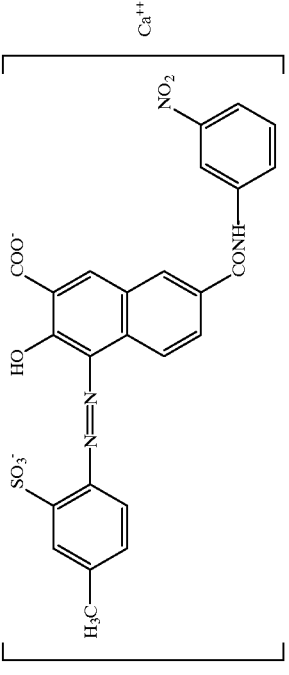 | Reddish purple | 462.7° C. (with decomposition) |
| 36 | 4-aminotoluene-3-sulfonic acid --------- 2-hydroxy-3-hydroxycarbonyl-6-(4'-nitrophenyl-aminocarbonyl)naphthalene | 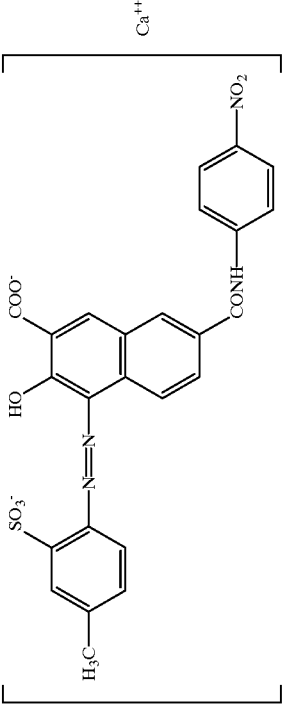 | Dark red | 462.7° C. (with decomposition) |
| 37 | 4-aminotoluene-3-sulfonic acid --------- 2-hydroxy-6-hydroxycarbonyl-3-phenylamino-carbonylnaphthalene | 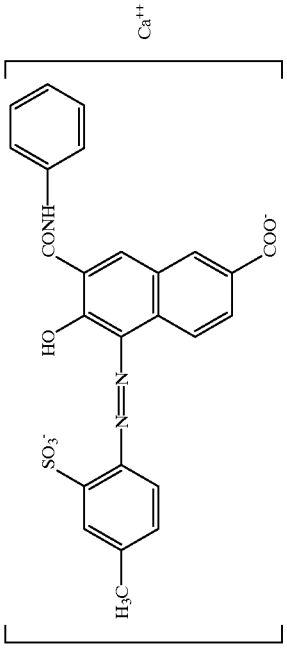 | Bluish purple | 458.5° C. (with decomposition) |

TABLE 3-continued

| Example No. | Amine (upper)/Coupler (lower) | Structural formula of azo compound | Color shade | Melting point/ decomposition point |
|---|---|---|---|---|
| 38 | 4-aminotoluene-3-sulfonic acid / 2-hydroxy-6-hydroxycarbonyl-3-(5'-chloro-2',4'-dimethoxyphenylaminocarbonyl)naphthalene | 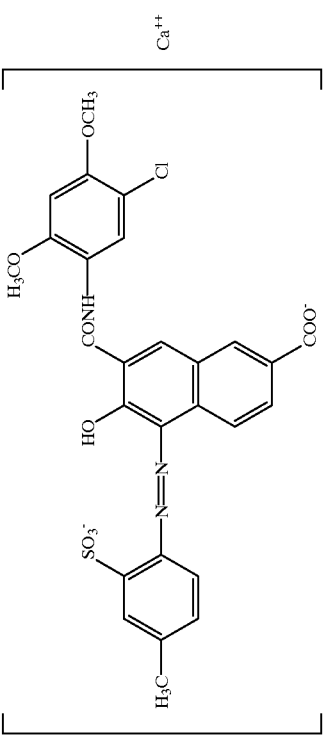 | Bluish red | 447.2° C. (with decomposition) |
| 39 | 4-aminotoluene-3-sulfonic acid / 2-hydroxy-6-hydroxycarbonyl-3-(3'-nitrophenyl-aminocarbonyl)naphthalene | 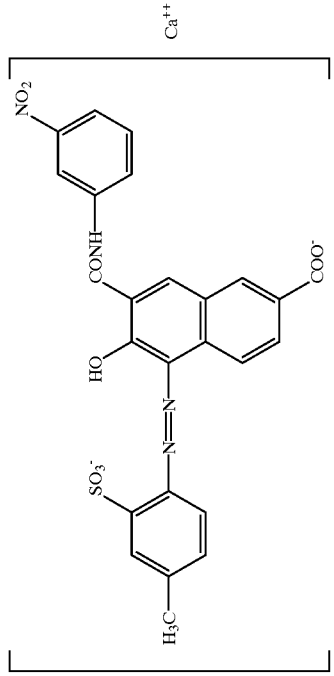 | Orange | 446.5° C. (with decomposition) |

TABLE 3-continued

| Example No. | Amine (upper)/Coupler (lower) | Structural formula of azo compound | Color shade | Melting point/ decomposition point |
|---|---|---|---|---|
| 40 | 4-aminotoluene-3-sulfonic acid --------- 2-hydroxy-6-hydroxycarbonyl-3-(3'-nitrophenyl-aminocarbonyl)naphthalene | 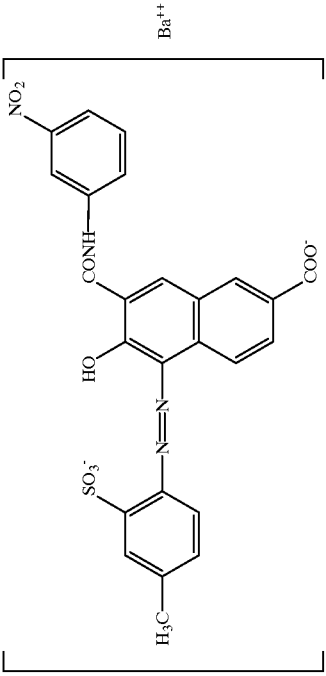 | Bluish red | 447.0° C. (with decomposition) |
| 41 | 4-aminotoluene-3-sulfonic acid --------- 2-hydroxy-6-hydroxycarbonyl-3-(3'-nitrophenyl-aminocarbonyl)naphthalene | 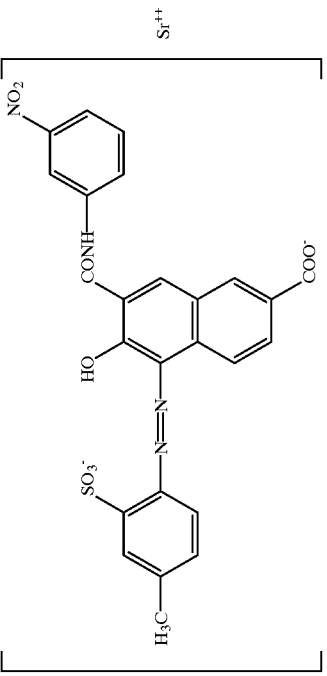 | Bluish red | 462.2° C. (with decomposition) |

TABLE 3-continued

| Example No. | Amine (upper)/Coupler (lower) | Structural formula of azo compound | Color shade | Melting point/ decomposition point |
|---|---|---|---|---|
| 42 | 4-aminotoluene-3-sulfonic acid --------- 2-hydroxy-6-hydroxycarbonyl-3-(3'-nitrophenyl-aminocarbonyl)naphthalene | [structure with Mn$^{++}$] | Dark bluish red | 428.7° C. (with decomposition) |
| 43 | 4-aminotoluene-3-sulfonic acid --------- 2-hydroxy-6-hydroxycarbonyl-3-(3'-nitrophenyl-aminocarbonyl)naphthalene | [structure with Ca$^{++}$] | Dark red | 465.6° C. (with decomposition) |

TABLE 3-continued

| Example No. | Amine (upper)/Coupler (lower) | Structural formula of azo compound | Color shade | Melting point/ decomposition point |
|---|---|---|---|---|
| 44 | 4-aminotoluene-3-sulfonic acid --------- 2-hydroxy-6-hydroxycarbonyl-3-(2'-chloro-5'-nitrophenylaminocarbonyl)naphthalene | [structure with Ca$^{++}$] | Yellowish red | 481.1° C. (with decomposition) |
| 45 | 4-aminotoluene-3-sulfonic acid --------- 2-hydroxy-6-hydroxycarbonyl-3-(2'-methyl-5'-nitrophenylaminocarbonyl)naphthalene | [structure with Ca$^{++}$] | Yellowish red | 455.8° C. (with decomposition) |
| 46 | 4-amino-2-chlorotoluene-5-sulfonic acid --------- 2-hydroxy-3,6-dihydroxycarbonylnaphthalene | [structure with 3/2 Ca$^{++}$] | Bluish red | 437.2° C. (with decomposition) |

TABLE 3-continued

| Example No. | Amine (upper)/Coupler (lower) | Structural formula of azo compound | Color shade | Melting point/ decomposition point |
|---|---|---|---|---|
| 47 | 4-amino-2-chlorotoluene-5-sulfonic acid ---------- 2-hydroxy-3-hydroxycarbonyl-6-phenylamino-carbonylnaphthalene | 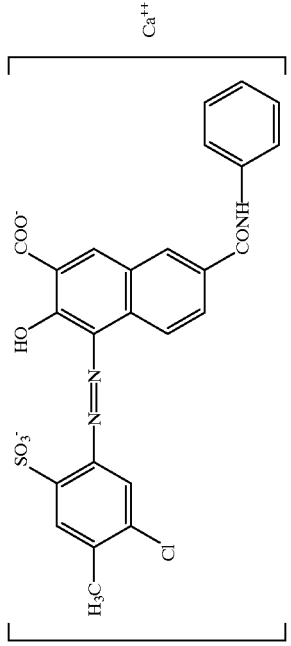 | Bluish red | 475.4° C. (with decomposition) |
| 48 | 4-amino-2-chlorotoluene-5-sulfonic acid ---------- 2-hydroxy-3-hydroxycarbonyl-6-(5'-chloro-2',4'-dimethoxyphenylaminocarbonyl)naphthalene | 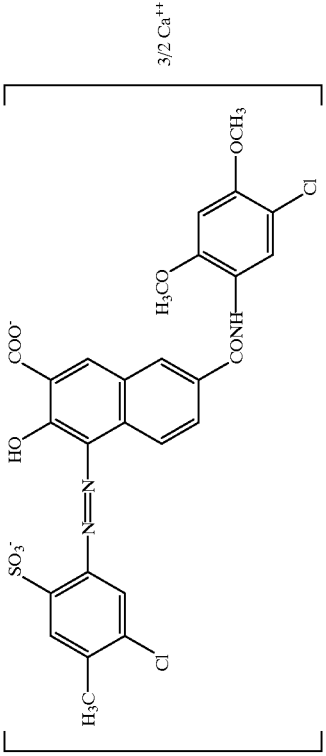 | Bluish red | 476.7° C. (with decomposition) |

TABLE 3-continued

| Example No. | Amine (upper)/Coupler (lower) | Structural formula of azo compound | Color shade | Melting point/decomposition point |
|---|---|---|---|---|
| 49 | 4-amino-2-chlorotoluene-5-sulfonic acid ---------- 2-hydroxy-3-hydroxycarbonyl-6-(3'-nitrophenyl-aminocarbonyl)naphthalene | 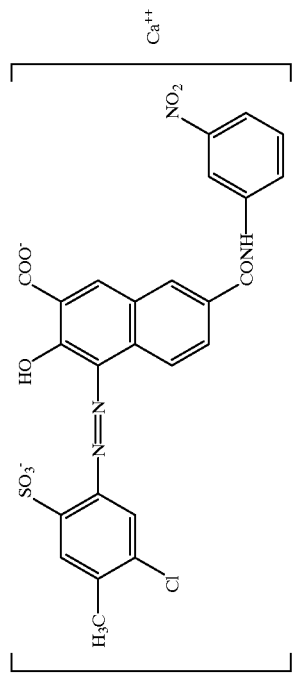 | Bluish red | 462.2° C. (with decomposition) |
| 50 | 4-amino-2-chlorotoluene-5-sulfonic acid ---------- 2-hydroxy-6-hydroxycarbonyl-3-phenylamino-carbonylnaphthalene | 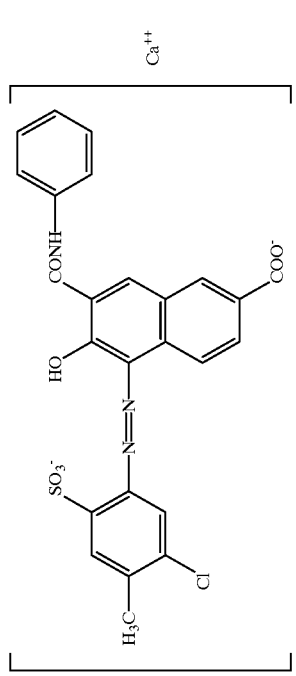 | Bluish red | 478.8° C. (with decomposition) |
| 51 | 4-amino-2-chlorotoluene-5-sulfonic acid ---------- 2-hydroxy-6-hydroxycarbonyl-3-(5'-chloro-2',4'-dimethoxyphenylaminocarbonyl)naphthalene | 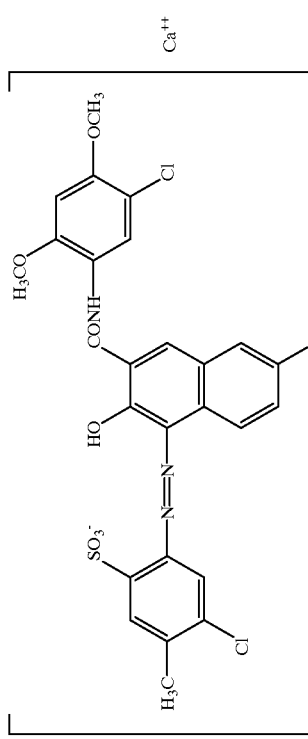 | Bluish red | 529.2° C. (with decomposition) |

TABLE 3-continued

| Example No. | Amine (upper)/Coupler (lower) | Structural formula of azo compound | Color shade | Melting point/ decomposition point |
|---|---|---|---|---|
| 52 | 4-amino-2-chlorotoluene-5-sulfonic acid<br>————<br>2-hydroxy-6-hydroxycarbonyl-3-(3'-nitrophenyl-aminocarbonyl)naphthalene | 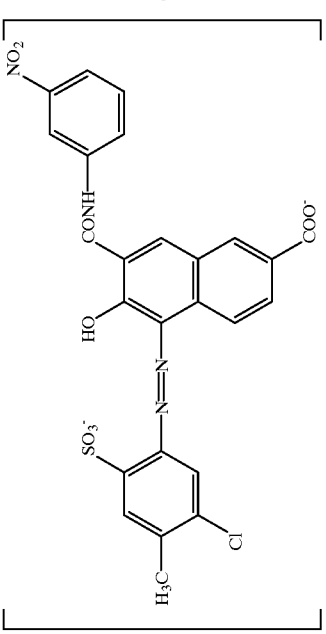 | Dark bluish red | 460.7° C. (with decomposition) |
| 53 | 5-amino-2-chlorotoluene-4-sulfonic acid<br>————<br>2-hydroxy-3,6-dihydroxycarbonylnaphthalene | 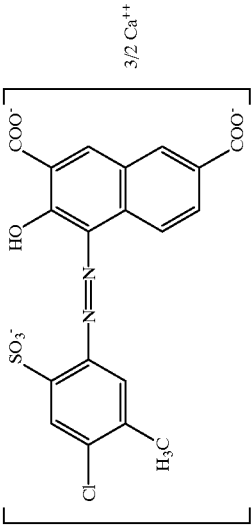 | Dark brownish red | 422.5° C. (with decomposition) |
| 54 | 5-amino-2-chlorotoluene-4-sulfonic acid<br>————<br>2-hydroxy-3-hydroxycarbonyl-6-phenylamino-carbonylnaphthalene | 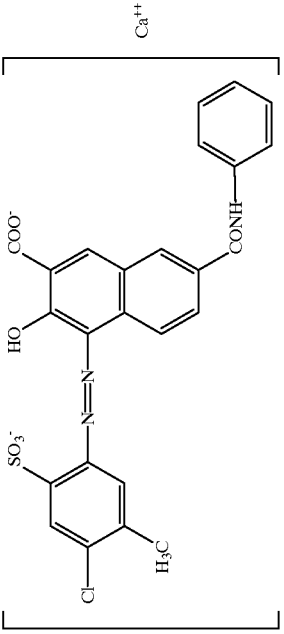 | Bluish red | 488.5° C. (with decomposition) |

TABLE 3-continued

| Example No. | Amine (upper)/Coupler (lower) | Structural formula of azo compound | Color shade | Melting point/ decomposition point |
|---|---|---|---|---|
| 55 | 5-amino-2-chlorotoluene-4-sulfonic acid ------- 2-hydroxy-3-hydroxycarbonyl-6-(5'-chloro-2',4'-dimethoxyphenylaminocarbonyl)naphthalene | (Ca²⁺ salt of azo compound) | Dark bluish red | 465.9° C. (with decomposition) |
| 56 | 5-amino-2-chlorotoluene-4-sulfonic acid ------- 2-hydroxy-3-hydroxycarbonyl-6-(3'-nitrophenyl-aminocarbonyl)naphthalene | (Ca²⁺ salt of azo compound) | Dark bluish red | 513.7° C. (with decomposition) |
| 57 | 5-amino-2-chlorotoluene-4-sulfonic acid ------- 2-hydroxy-6-hydroxycarbonyl-3-phenylamino-carbonylnaphthalene | (Ca²⁺ salt of azo compound) | Bluish red | 480.0° C. (with decomposition) |

TABLE 3-continued

| Example No. | Amine (upper)/Coupler (lower) | Structural formula of azo compound | Color shade | Melting point/ decomposition point |
|---|---|---|---|---|
| 58 | 5-amino-2-chlorotoluene-4-sulfonic acid --------- 2-hydroxy-6-hydroxycarbonyl-3-(5'-chloro-2',4'-dimethoxyphenylaminocarbonyl)naphthalene | 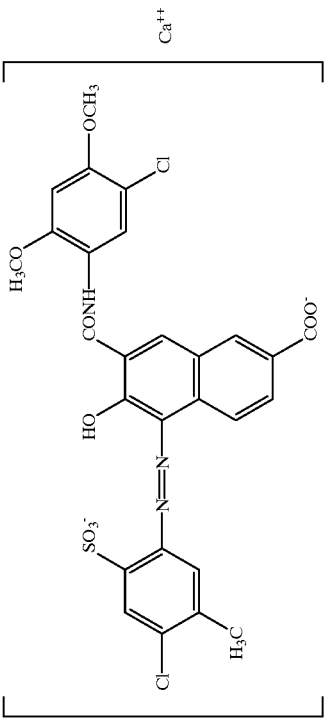 | Bluish red | 461.8° C. (with decomposition) |
| 59 | 5-amino-2-chlorotoluene-4-sulfonic acid --------- 2-hydroxy-6-hydroxycarbonyl-3-(3'-nitro-phenylaminocarbonyl)naphthalene | 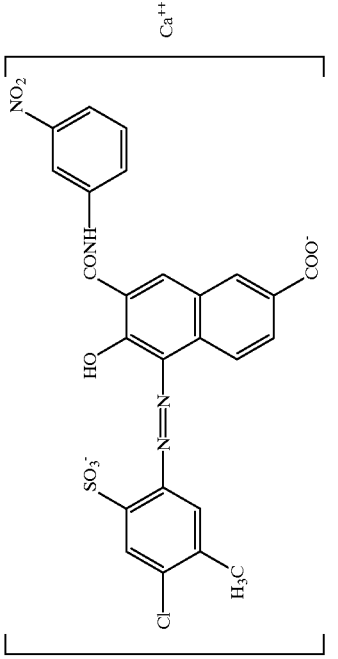 | Bluish red | 465.3° C. (with decomposition) |

TABLE 3-continued

| Example No. | Amine (upper)/Coupler (lower) | Structural formula of azo compound | Color shade | Melting point/ decomposition point |
|---|---|---|---|---|
| 60 | 2-amino-1-naphthalene-sulfonic acid --------- 2-hydroxy-3,6-dihydroxycarbonylnaphthalene | [Structure: naphthalene-SO₃⁻ linked via N=N to naphthalene with OH, COO⁻, COO⁻ substituents; 3/2 Ca²⁺] | Reddish purple | 438.3° C. (with decomposition) |
| 61 | 2-amino-1-naphthalene-sulfonic acid --------- 2-hydroxy-3-hydroxycarbonyl-6-phenylamino-carbonylnaphthalene | [Structure: naphthalene-SO₃⁻ linked via N=N to naphthalene with OH, COO⁻, CONH-phenyl substituents; Ca²⁺] | Dark Bluish purple | 474.5° C. (with decomposition) |
| 62 | 2-amino-1-naphthalene-sulfonic acid --------- 2-hydroxy-3-hydroxycarbonyl-6-(5'-chloro-2',4'-dimethoxyphenylaminocarbonyl)naphthalene | [Structure: naphthalene-SO₃⁻ linked via N=N to naphthalene with OH, COO⁻, CONH-(5-chloro-2,4-dimethoxyphenyl) substituents; Ca²⁺] | Dark Bluish purple | 486.7° C. (with decomposition) |

TABLE 3-continued

| Example No. | Amine (upper)/Coupler (lower) | Structural formula of azo compound | Color shade | Melting point/decomposition point |
|---|---|---|---|---|
| 63 | 2-amino-1-naphthalene-sulfonic acid ------------ 2-hydroxy-3-hydroxycarbonyl-6-(3'-nitro-phenyl)aminocarbonyl)- | 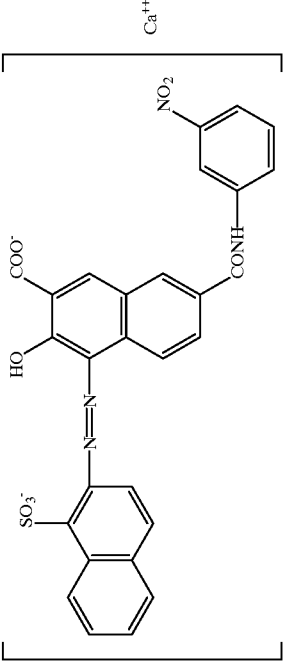 | Dark Bluish purple | 564.9° C. (with decomposition) |
| 64 | 2-amino-1-naphthalene-sulfonic acid ------------ 2-hydroxy-6-hydroxycarbonyl-3-phenylamino-carbonylnaphthalene | 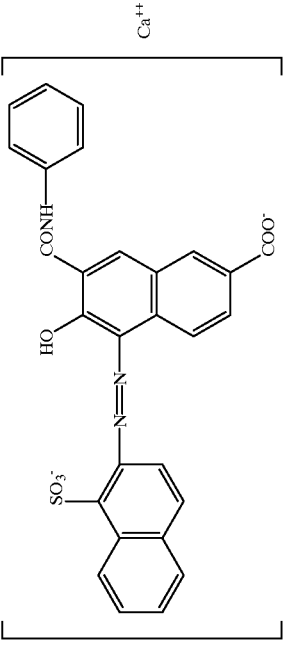 | Dark purple | 507.1° C. (with decomposition) |
| 65 | 2-amino-1-naphthalene-sulfonic acid ------------ 2-hydroxy-6-hydroxycarbonyl-3-(5'-chloro-2',4'-dimethoxyphenylaminocarbonyl)naphthalene | 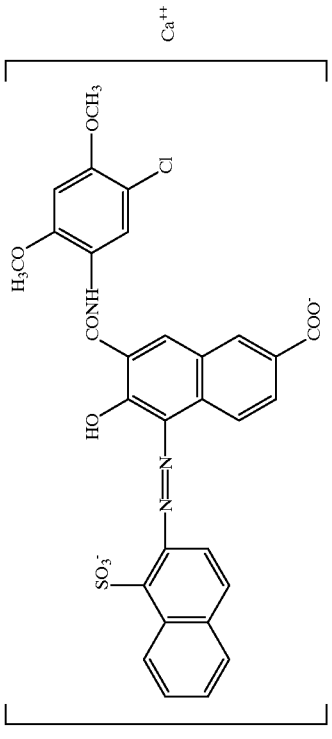 | Dark purple | 530.6° C. (with decomposition) |

TABLE 3-continued

| Example No. | Amine (upper)/Coupler (lower) | Structural formula of azo compound | Color shade | Melting point/decomposition point |
|---|---|---|---|---|
| 66 | 2-amino-1-naphthalene-sulfonic acid / 2-hydroxy-6-hydroxycarbonyl-3-(3'-nitro-phenylaminocarbonyl)naphthalene | 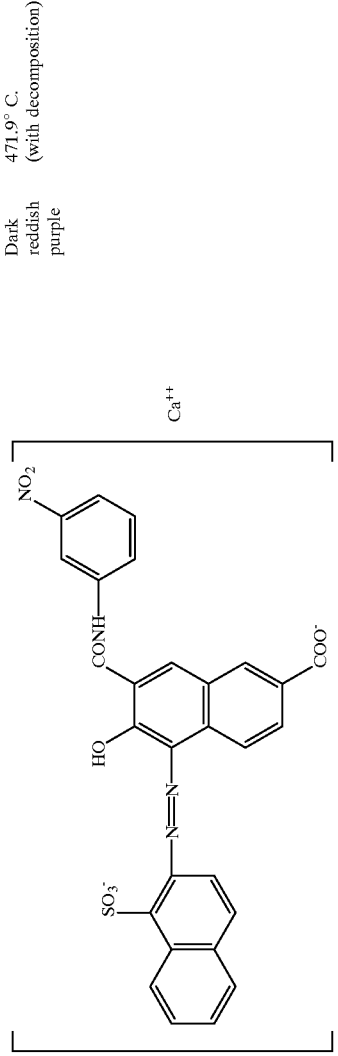 | Dark reddish purple | 471.9° C. (with decomposition) |
| 67 | 2-nitroaniline-4-sulfonic acid / 2-hydroxy-3,6-dihydroxycarbonylnaphthalene | 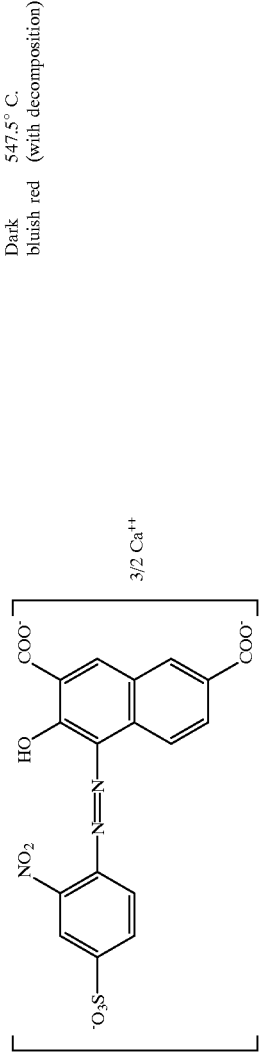 | Dark bluish red | 547.5° C. (with decomposition) |
| 68 | 2-nitroaniline-4-sulfonic acid / 2-hydroxy-3-hydroxycarbonyl-6-phenylamino-carbonylnaphthalene | 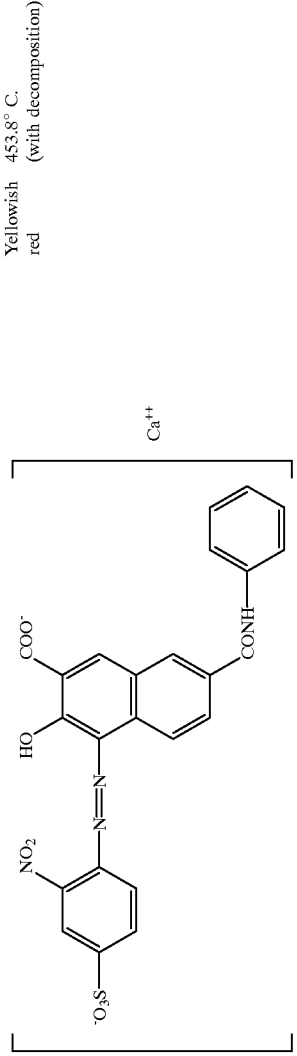 | Yellowish red | 453.8° C. (with decomposition) |

TABLE 3-continued

| Example No. | Amine (upper)/Coupler (lower) | Structural formula of azo compound | Color shade | Melting point/ decomposition point |
|---|---|---|---|---|
| 69 | 2-nitroaniline-4-sulfonic acid ---------- 2-hydroxy-3-hydroxycarbonyl-6-(5'-chloro-2',4'-dimethoxyphenylaminocarbonyl)naphthalene | 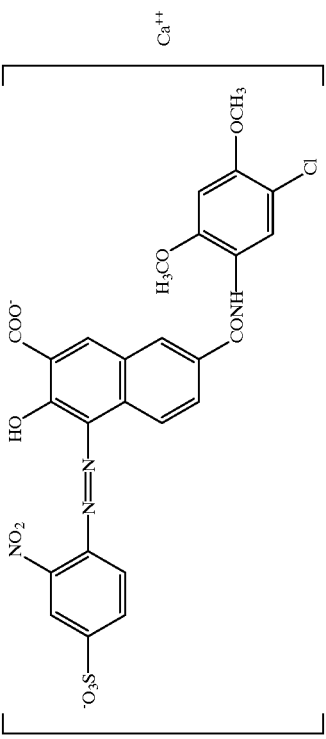 | Brownish red | 435.7° C. (with decomposition) |
| 70 | 2-nitroaniline-4-sulfonic acid ---------- 2-hydroxy-3-hydroxycarbonyl-6-(3'-nitrophenylaminocarbonyl)naphthalene | 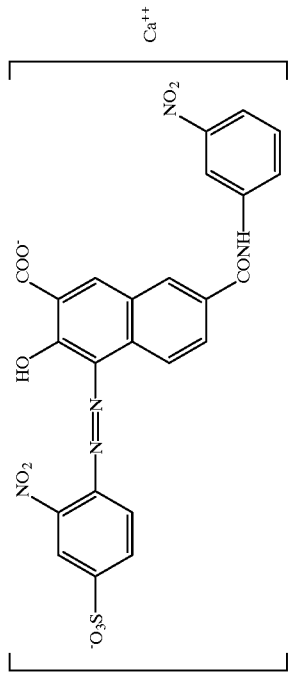 | Yellowish red | 443.3° C. (with decomposition) |
| 71 | 2-nitroaniline-4-sulfonic acid ---------- 2-hydroxy-6-hydroxycarbonyl-3-phenylaminocarbonylnaphthalene | 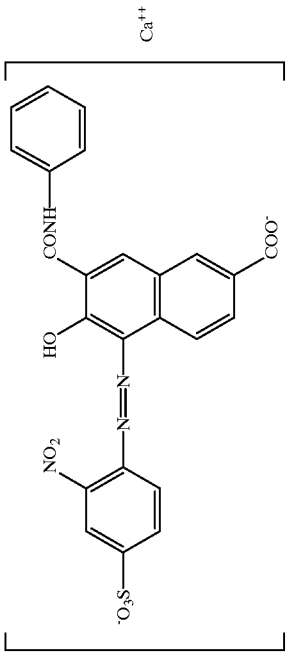 | Brownish red | 450.1° C. (with decomposition) |

TABLE 3-continued

| Example No. | Amine (upper)/Coupler (lower) | Structural formula of azo compound | Color shade | Melting point/ decomposition point |
|---|---|---|---|---|
| 72 | 2-nitroaniline-4-sulfonic acid ——————— 2-hydroxy-6-hydroxycarbonyl-3-(5'-chloro-2',4'-dimethylphenylaminocarbonyl)naphthalene | 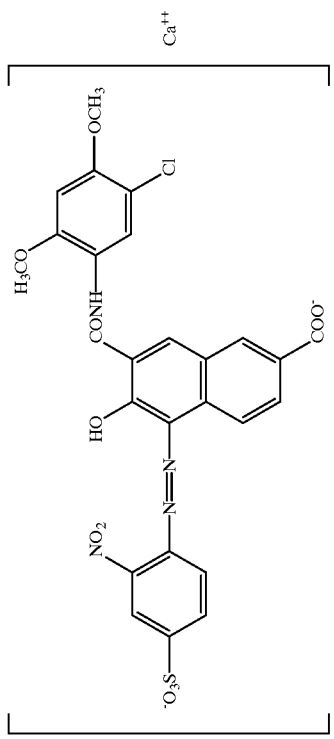 | Dark brownish red | 434.9° C. (with decomposition) |
| 73 | 2-nitroaniline-4-sulfonic acid ——————— 2-hydroxy-6-hydroxycarbonyl-3-(3'-nitro-phenylaminocarbonyl)naphthalene | 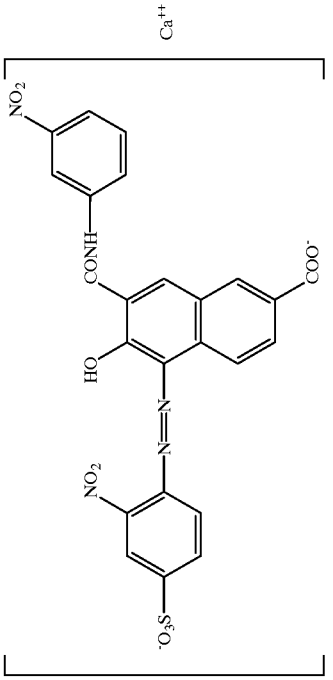 | Bluish red | 430.5° C. (with decomposition) |

EXPERIMENT EXAMPLE

With respect to azo compounds obtained in Examples 39, 54 and 64, each printing ink was prepared according to JIS K5101 and a color is extended. The color data are shown in Table 4. As the color data, the dominant wavelength ($\lambda_d$), the excitation purity ($p_e$) and the brightness (Y) defined in JIS Z8701 are shown.

TABLE 4

|  | Dominant wavelength $\lambda_d$(nm) | Excitation purity $P_e$(%) | Brightness Y (%) |
|---|---|---|---|
| Example 39 | 610 | 58.1 | 14.5 |
| Example 54 | 619 | 47.6 | 8.5 |
| Example 64 | 645 | 32.2 | 6.8 |

EXAMPLE 74

Synthesis of 2-hydroxy-1-(2'-methoxy-5'phenylaminocarbonylphenyl)azo-3-methoxycarbonyl-6-(3"-nitrophenyl)aminocarbonylnaphthalene

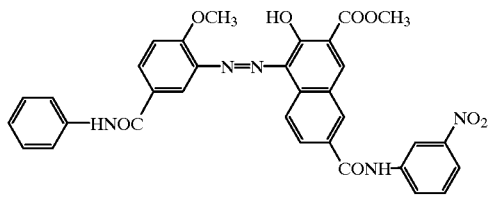

According to the same manner as described in Example 27(2) except for replacing 2-hydroxy-3,6-bis(benzothiazol-2'-ylaminocarbonyl)naphthalene of Example 27(2) by 1.10 g of 2-hydroxy-3-methoxycarbonyl-6-(3'-nitrophenyl)aminocarbonylnaphthalene as a coupler component, 1.44 g of a red powder [2-hydroxy-1-(2'-methoxy-5'-phenylaminocarbonylphenyl)azo-3-methoxycarbonyl-6-(3"-nitrophenyl)aminocarbonylnaphthalene] was obtained (melting point·decomposition point: 315.8° C. (with decomposition)).

EXAMPLE 75

Synthesis of 2-hydroxy-1-(2'-methoxy-5'-phenylaminocarbonylphenyl)azo-3-methoxycarbonyl-6-benzyloxycarbonylnaphthalene

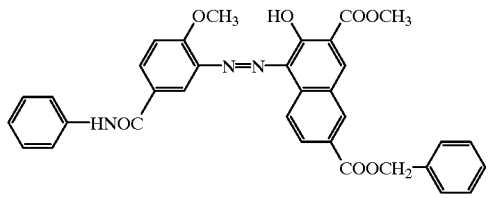

According to the same manner as described in Example 27(2) except for replacing 2-hydroxy-3,6-bis(benzothiazol-2'-ylaminocarbonyl)naphthalene of Example 27(2) by 1.01 g of 2-hydroxy-3-methoxycarbonyl-6-benzyloxycarbonylnaphthalene as a coupler component, 1.42 g of a red powder [2-hydroxy-1-(2'-methoxy-5'-phenylaminocarbonylphenyl)azo-3-methoxycarbonyl-6-benzyloxycarbonylnaphthalene] was obtained (melting point·decomposition point: 332.6° C. (with decomposition)).

EXAMPLE 76

Synthesis of 2-hydroxy-1-(2'-methoxy-5'-phenylaminocarbonylphenyl)azo-3,6-bis(phenoxycarbonyl) naphthalene

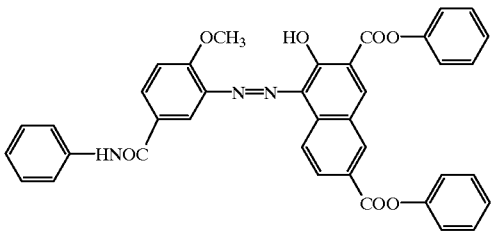

According to the same manner as described in Example 27(2) except for replacing 2-hydroxy-3,6-bis(benzothiazol-2'-ylaminocarbonyl)naphthalene of Example 27(2) by 1.15 g of 2-hydroxy-3,6-bis(phenoxycarbonyl)naphthalene as a coupler component, 1.23 g of a red powder [2-hydroxy-1-(2'-methoxy-5'-phenylaminocarbonylphenyl)azo-3,6-bis (phenoxycarbonyl)naphthalene] was obtained (melting point·decomposition point: 328.8° C. (with decomposition)).

EXAMPLE 77

Synthesis of 2-methoxy-1-(2'-methoxy-5'-phenylaminocarbonylphenyl)azo-3-(benzimidazolon-5"-ylaminocarbonyl)-6-phenylaminocarbonylnaphthalene

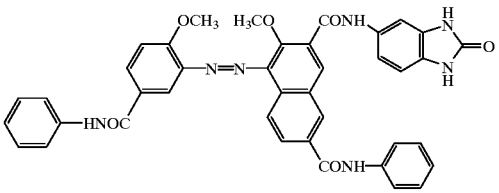

According to the same manner as described in Example 27(2) except for replacing 2-hydroxy-3,6-bis(benzothiazol-2'-ylaminocarbonyl)naphthalene of Example 27(2) by 0.95 g of 2-methoxy-3-(benzimidazolon-5"-ylaminocarbonyl)-6-phenylaminocarbonylnaphthalene as a coupler component, and changing the stirring time to 100 hours or more, 0.41 g of a dark subdued red powder [2-methoxy-1-(2'-methoxy-5'-phenylaminocarbonylphenyl)azo-3-benzimidazolon-5"-ylaminocarbonyl)-6-phenylaminocarbonylnaphthalene] was obtained (melting point·decomposition point: 314.3° C. (with decomposition)).

EXAMPLE 78

Synthesis of 2-methoxy-1-(4'-nitrophenylazo)-3-(benzimidazolon-5"-ylaminocarbonyl)-6-phenylaminocarbonylnaphthalene

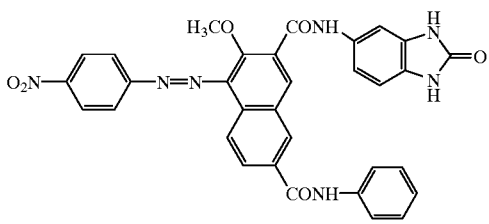

According to the same manner as described in Example 77 except for replacing 2-methoxy-5-phenylaminocarbonylaniline of Example 77 by 0.42 g of 4-nitroaniline as an amine component, 1.12 g of a bluish red powder [2-methoxy-1-(4'-nitrophenylazo)-3-(benzimidazolon-5"-ylaminocarbonyl)-6-phenylaminocarbonylnaphthalene] was obtained (melting point·decomposition point: 323.3° C. (with decomposition)).

The azo compound of the present invention is characterized by having two carboxyl groups (which may form a salt), carboxyamides, carboxyureides or esters at the 3- and 6-positions of 2-hydroxynaphthalene as a coupler. The coloring material obtained from the compound shows higher solvent resistance, water resistance and chemical resistance in comparison with the case of using a coupler having these groups in other positions of 2-hydroxynaphthalene, or the case of having one carboxyamide, carboxyureide or ester.

Figure 1:
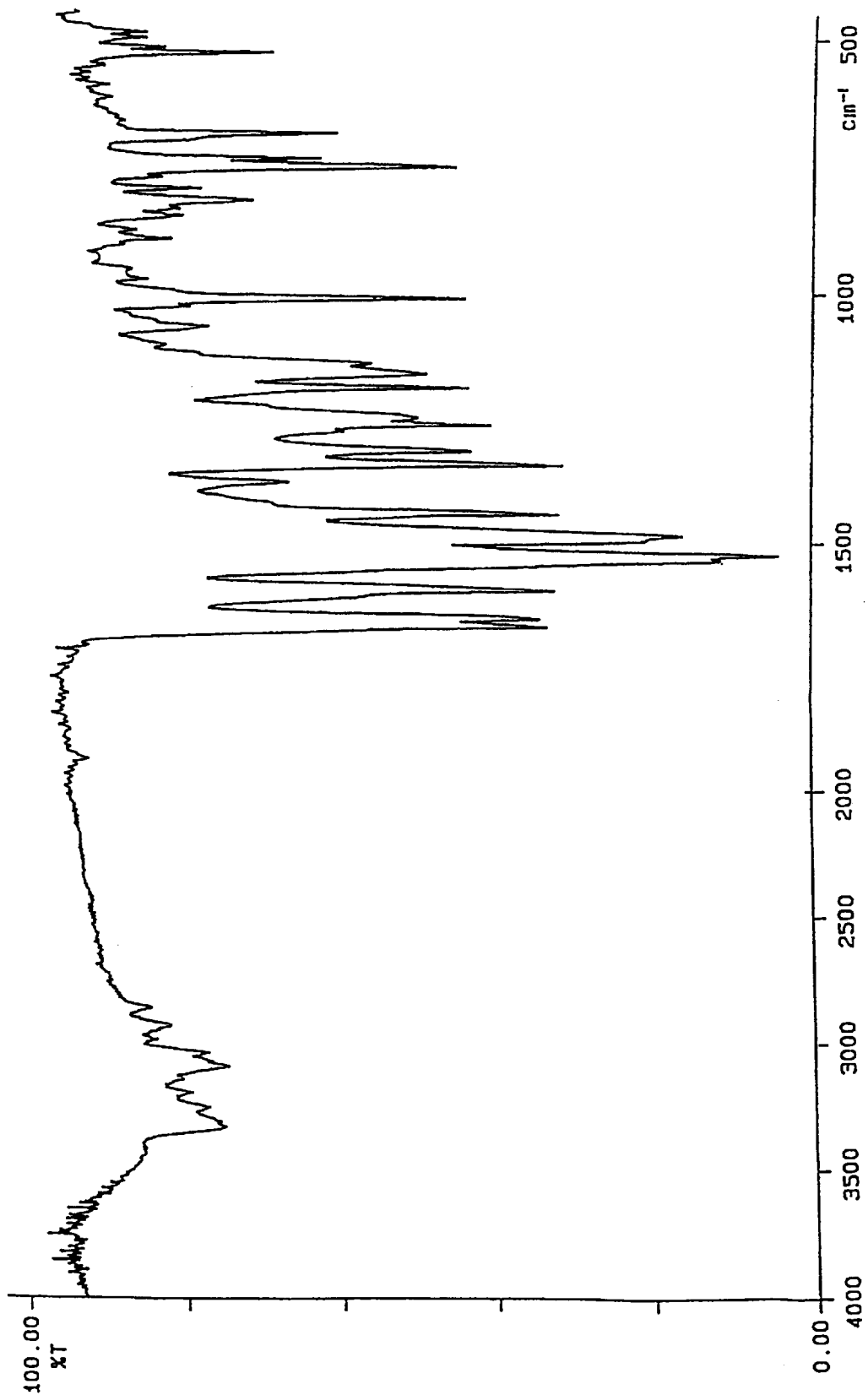
FIG. 1 shows an infrared absorption spectrum of the azo compound of Example 1.
Figure 2:
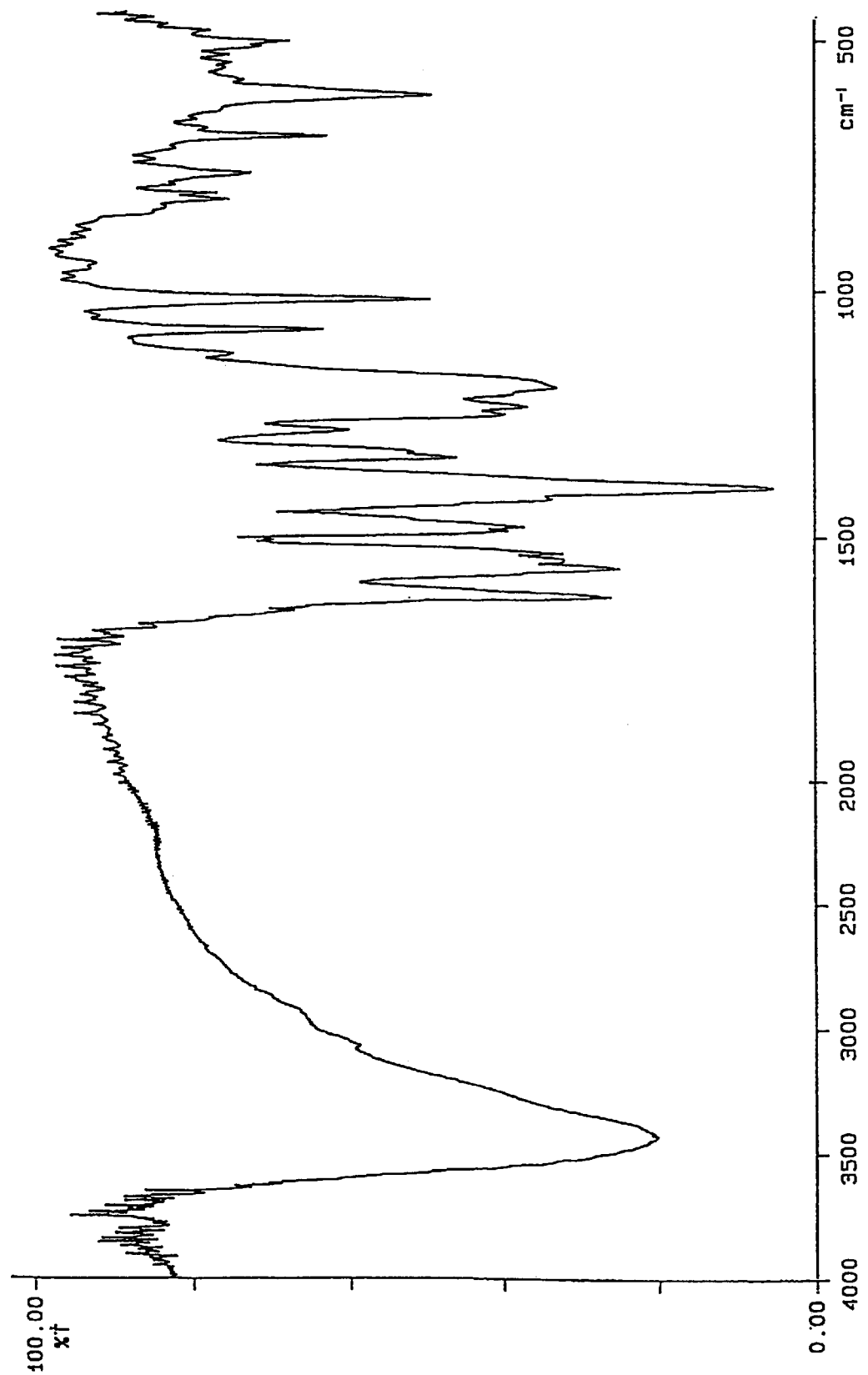
FIG. 2 shows an infrared absorption spectrum of the calcium salt of the azo compound of Example 23, respectively.

We claim:

1. An azo compound represented by the following general formula I:

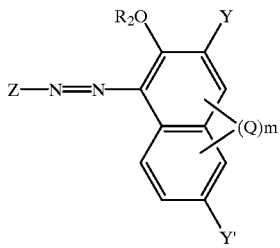

wherein Y represents —(CONH)n—X or —COR;
Y' represents —(CONH)n—X' or —COR';
(X and X' may be the same or different and represent an optionally substituted aromatic group, or an optionally substituted heterocyclic group having a conjugated double bond);
R and R' may be the same or different and represent a hydroxyl group, an optionally branched alkoxy group having 1 to 6 carbon atoms, a benzyloxy group, a phenyloxy group or a phenacyloxy group (provided that an acceptable salt may be formed when any one of R and R' is a hydroxyl group);
n represents an integer of 1 or 2;
$R_2$ represents a hydrogen atom, an optionally branched alkyl group having 1 to 6 carbon atoms, an acyl group having 1 to 6 carbon atoms, or a phenylalkyl group;
Q represents an optionally branched alkyl group having 1 to 6 carbon atoms, an optionally branched alkoxyl group having 1 to 6 carbon atoms, a halogen atom, a nitro group or a nitroso group; m represents an integer of 0 to 3 (when m is 1, Q may be combined with any one of two condensed rings and, when m is 2 or 3, Q may be combined with one or both condensed rings or may be combined together with two condensed rings to form a ring); and
Z represents an optionally substituted monovalent aromatic group.

2. The azo compound according to claim 1, wherein Y is —(CONH)n—X, and Y' is —(CONH)n—X' (n, X and X' are defined as above).

3. The azo compound according to claim 1, wherein Z is a phenyl group or a naphthyl group.

4. A pigment comprising the azo compound of claim 1.

5. A printing ink comprising the azo compound of claim 1.

6. A coating composition comprising the azo compound of claim 1.

7. A colorating agent for plastics, comprising the azo compound of claim 1.

8. A process for producing the azo compound of claim 1, which comprises diazotizing an aromatic amine represented by the following general formula II:

$$Z-NH_2 \qquad \qquad II$$

wherein Z represents an optionally substituted monovalent aromatic group and coupling the resulting diazonium compound with a compound represented by the following formula III:

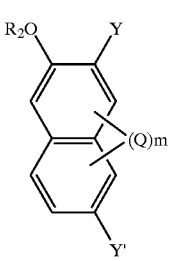

wherein Y represents —(CONH)n—X or —COR;
Y' represents —(CONH)n—X' or —COR';
(X and X' may be the same or different and represent an optionally substituted aromatic group, or an optionally substituted heterocyclic group having a conjugated double bond);
R and R' may be the same or different and represent a hydroxyl group, an optionally branched alkoxy group having 1 to 6 carbon atoms, a benzyloxy group, a phenyloxy group or a phenacyloxy group;
n represents an integer of 1 or 2; and
$R_2$ represents a hydrogen atom, an optionally branched alkyl group having 1 to 6 carbon atoms or an acyl group having 1 to 6 carbon atoms or a phenylalkyl group; and
Q represents an optionally branched alkyl group having 1 to 6 carbon atoms, an optionally branched alkoxyl group having 1 to 6 carbon atoms, a halogen atom, a nitro group or a nitroso group; m represents an integer of 0 to 3 (when m is 1, Q may be combined with any one of two condensed rings and, when m is 2 or 3, Q may be combined with one or both condensed rings or may be combined together with two condensed rings to form a ring) (provided that a lake may be formed by optionally reacting the resultant azo compound with a metallic salt, when R or R' is a hydroxyl group).

9. The process according to the claim 8, wherein Z is a phenyl group or naphthyl group.

* * * * *